(12) United States Patent
Taheri et al.

(10) Patent No.: US 8,080,215 B2
(45) Date of Patent: Dec. 20, 2011

(54) FLOW REACTORS FOR CHEMICAL CONVERSIONS WITH HETEROGENEOUS CATALYSTS

(75) Inventors: Hassan Taheri, Naperville, IL (US); Curtis D. Dickinson, Mahomet, IL (US); Paul A. Jacobson, Batavia, IL (US)

(73) Assignee: BP Corporation North America Inc., Warrenville, IL (US)

( * ) Notice: Subject to any disclaimer, the term of this patent is extended or adjusted under 35 U.S.C. 154(b) by 388 days.

(21) Appl. No.: 11/999,296

(22) Filed: Dec. 4, 2007

(65) Prior Publication Data

US 2009/0043114 A1    Feb. 12, 2009

Related U.S. Application Data

(62) Division of application No. 09/920,981, filed on Aug. 2, 2001, now Pat. No. 7,316,804.

(51) Int. Cl.
    *B01J 8/04*      (2006.01)
    *B01J 8/06*      (2006.01)
(52) U.S. Cl. ........................................ 422/211; 422/201
(58) Field of Classification Search .................. 422/197, 422/198, 211, 201, 191
See application file for complete search history.

(56) References Cited

U.S. PATENT DOCUMENTS

| | | | |
|---|---|---|---|
| 4,472,527 A | 9/1984 | Otake et al. | |
| 4,520,127 A | 5/1985 | Otake et al. | |

FOREIGN PATENT DOCUMENTS

| | | | |
|---|---|---|---|
| DE | 2929300 | * | 1/1981 |
| WO | WO 03/011449 | * | 2/2003 |

* cited by examiner

*Primary Examiner* — Bernard Dentz
(74) *Attorney, Agent, or Firm* — Nixon & Vanderhye

(57) ABSTRACT

Flow reactor having a plurality of walled conduits each having an outer surface disposed for contact with a heat-transfer medium, an inlet distribution manifold in flow communication with a downstream manifold through channels formed by heterogeneous catalytic material disposed within each conduit during operation, and a sequence of zones comprising at least two zones, the zones including the walled conduits. The walled conduits within each zone have the same or different length measured along a longitudinal coordinate of the zone, the walled conduits within each zone have essentially uniform cross-section measured in a plane perpendicular to the longitudinal coordinate thereby defining volume of the zone, and in the sequence of zones, the total cross-sectional area of the conduits in each downstream zone varies from the prior upstream zone. At least one crossover chamber is provided in flow communication with the plurality of walled conduits of a downstream zone and the plurality of walled conduits of the prior upstream zone. A shell is present for maintaining during operation the outer surface the plurality of walled conduits of each zone predominantly in contact with a heat transfer medium, the shell having an inlet in flow communication with an outlet for flow of the heat-transfer medium.

12 Claims, 5 Drawing Sheets

FLOW REACTORS FOR CHEMICAL CONVERSIONS WITH HETEROGENEOUS CATALYSTS

This application is a divisional of application Ser. No. 09/920,981, filed Aug. 2, 2001, now U.S. Pat. No. 7,316,804.

TECHNICAL FIELD

The present invention relates to apparatus for use in process systems which include exothermic chemical conversions of organic compounds to value added products. More particularly, the invention is flow reactors for exothermic chemical conversions using a fixed heterogeneous catalyst with means for control of the exotherm.

Flow reactors of the invention comprise a plurality of walled conduits each having an outer surface disposed for contact with a heat-transfer medium, an inlet distribution manifold adapted for flow communication with a downstream manifold through channels formed by heterogeneous catalytic material disposed within each conduit during operation in a sequence of zones for catalyst having the same or different length along the longitudinal coordinate of the conduit and within each zone essentially uniform cross-section of the conduit measured in a plane perpendicular to the longitudinal coordinate thereby defining volume of the zone, and the sequence of zones comprising a plurality of zones such that each downstream zone has a varying (i.e. larger or smaller) cross-section than the contiguous upstream zone. Reactors of the invention generally comprise a shell adapted to maintain during operation the outer surface of each conduit predominantly in contact with a heat-transfer medium, and having an inlet in flow communication with an outlet for the heat-transfer medium.

Another aspect of the invention includes chemical processes which use such flow reactors comprising a plurality of zones such that each downstream zone has a varying cross-section than the contiguous upstream zone. Such processes include, for example, the continuous manufacture of maleic acid's intramolecular anhydride, commonly referred to as maleic anhydride wherein each downstream zone has a larger cross-section than the contiguous upstream zone.

BACKGROUND OF THE INVENTION

In most, if not all, processes involving chemical conversions the control of temperature by means for transfer of energy is very important, because chemical reactions either absorb or evolve energy. Where highly exothermic reactions are carried out in a flow reactor containing a fixed heterogeneous catalyst, energy evolved near the entrance of the reactants in contact with the catalyst is well-known to cause non-isothermal conditions which can result in deleterious overheating of the catalyst. Furthermore, non-isothermal conditions of reaction are likely to decrease desired conversions, throughput, and/or yields of value added products.

In a large class of industrial processes the conventional design of reaction apparatus applicable for use in carrying out highly exothermic chemical reactions uses an annular bundle of vertical contact tubes which are adapted to contain a fixed heterogeneous catalyst. Reaction gases are directed through the tubes containing the catalyst and the heat evolved as the reaction proceeds is removed by a heat carrier which is circulated over the outer surface of the contact tubes.

Conventional flow reactors are illustrated in FIG. 1. Typically, such reactors comprise a plurality of walled conduits each having an outer surface disposed for contact with a heat-transfer medium, and an inlet distribution manifold adapted for flow communication with a downstream manifold. The conduits are of uniform cross-section throughout the length of the reactor. In such reactors, it is sometimes difficult to balance the heat generated during the reaction with the heat removal capabilities of the heat transfer medium. The result is that such reactors may operate with a "hot spot" (i.e. the location in the catalyst bed wherein the exothermic reaction exceeds the heat removal capabilities of the reactor), or "runaway reactions" (because of insufficient heat removal and often wherein oxygen is a reactant, the reactants and preferred products continue to oxidize or combust to non product chemical compounds). Either of these occurrences often leads to an irreversible chemical or physical damage of the catalyst and/or drastically reduces the life and/or performance of the catalyst. Specifically, the catalyst may melt and/or fuse together; the catalyst crystal structure or composition may be altered, any of which can cause the loss of activity and/or selectivity of the catalyst to preferred products.

Many designs directed to an improved heat exchange arrangement for such reaction apparatus are known.

For example, U.S. Pat. No. 3,850,233 in the name of Oskar Wanka and Jeno Mihaleyi describes reaction apparatus which is a compact structure of a closed type, without external portions, but with a complex internal arrangement including a pump which directs a flow of heat carrier medium along an inner tubular baffle toward the opposite end and then through an opening in the inner tubular baffle over the contact tubes and then back toward the pump for return through an annular space between an annular baffle and the inner tubular baffle. This complex internal arrangement is said to provide a most favorable flowing course for the heat carrier and a desirable heat exchange relationship between the different media for endothermic chemical processes.

U.S. Pat. No. 3,871,445 in the name of Oskar Wanka, Friedrich Gutlhuber and Hermann Graf describes conventional design of reaction apparatus for carrying out exothermic and endothermic chemical reactions, having a shell in which there is arranged a vertical next of contact tubes. These contact tubes, which contain a catalyst material, have their opposite ends secured, in a fluid-tight manner, into respective headers and open, at their opposite ends, into upper and lower heads connected to the shell, reaction gases flowing through the contact tubes are supplied and removed through these heads. According to the patent, a heat exchange medium is pumped through an external heat exchanger and is supplied and discharged to the shell through respective axially spaced annular supply and discharge conduits, to flow over the contact tubes. Baffles are arranged in the shell to extend transversely to the length of the tubes to direct the heat exchange medium to flow alternately in opposed radial directions over the tubes between the supply and discharge conduits. At least one additional annular circuit is arranged at a point of the shell intermediate between the supply and discharge conduits, is connected to the heat exchanger and the shell, and supplies and discharges a partial amount of the heat exchange medium. In one of these complex examples, several such additional annular conduits are arranged at respective points of the shell intermediate between the supply and discharge conduits. In another, diaphragms or partitions divide the shell side into separate compartments each of which has a respective heat exchanger associated therewith.

More recently, U.S. Pat. No. 3,871,445 in the name of Oskar Wanka, Friedrich Gutlhuber and Cedomil Persic describes a multistage reaction apparatus for carrying out exothermic or endothermic catalyst reactions comprising a plurality of separate stages which are arranged sequentially within the reaction vessel and consecutively passed through by the reaction gas. Each stage includes a separately removable module filled with a catalyst, and a gas cooler in the form of a heat exchanger mounted downstream of the module. Each heat exchanger represents a controllable partial cooling circuit and all of the exchangers are interconnected by a common circulation system serving to balance out larger temperature variations and to supply the partial circuits. The common circuit, including a man heat exchanger and a pump mounted in the return branch or branches of the circuit and the partial circuits or exchangers are controlled by valves or three-way control members and may also each comprise a pump. According to the patent such complex multistage reaction apparatus for carrying out exothermic or endothermic catalytic reactions in which the reaction gas subsequently passes through several beds of catalysts placed in transversely arranged cases and is cooled down or heated up in each such stage by means of a heat exchanger whose partial medium circuit is controllable by valves or three-way control members and with the aid of a main circulation system is thereby capable to hold the temperature of the reaction gas uniformly distributed over the cross-section of the reactor and, at the entrance of the stages, on the substantially same level.

U.S. Pat. No. 4,657,741 in the name of Rudolf Vogl, describes a reactor for carrying out exothermic and endothermic catalytic reactions which includes a contact tube bundle and radial admission and removal of a heat transfer medium via an annular duct for each, and a circulation through an external heat exchanger. Two or more circulating pumps are connected to the annular ducts and are distributed over the circumference. The heat exchanger can be arranged in shunt to the main circulation and be connected with individual sections of at least one annular duct via setting elements.

In U.S. Pat. No. 5,161,605 in the name of Friedrich Gutlhuber a tubular reactor for catalytic gas-phase reactions is described with symparallel (sic) guidance of the heat exchanger. A partial stream of the heat-exchanger medium, immediately neighboring the inlet side of the tube plate, is introduced through a by-pass channel arranged in the center of the bank of tubes, by-passing the bank of tubes, and at a point downstream of the discharge area of the heat-exchanger. In this way, according to the patent, undesirable severe local cooling in the reaction area of the bank of tubes can be avoided.

All the above-described methods are essentially based on modifying the heat transfer from the contact tubes which contain heterogeneous catalyst after this heat has been produced by the chemical conversion reactions therein. In a paper titled, "An Alternative Method to Control the Longitudinal Temperature Profile in Packed Tubular Reactions (ING. CHIM. ITAL., v. 12, n. 1-2, pp. 516, gennaio-febbraio 1976) authors P. Fontana and B. Canepa credit P. H. Chalderbank, A. Caldwell and G. Ross as suggesting another method whereby the heat generation rate is controlled at the source, by mixing catalyst-containing pellets and inert pellets invariable ratio along the axial co-ordinate. See "Proceedings of the 45th European Symposium on Chemical Reaction Engineering" (Pergamon Press, London 1971). Charging a plurality of contact tubes with a mixture of catalyst-containing pellets and inert pellets according to a prescribed variable ratio along the axial co-ordinate, clearly complicates the loading process as well as recovery of catalyst values from deactivated catalyst. Whether or not such a method could in any way be more useful than previous described methods, it is clearly based on the regulation of the heat produced per unit of time and volume of the bed without altering the means for transfer of such heat from the outer surface of the tubes.

Authors Fontana and Canepa direct their paper to a method of obtaining a predetermined axial temperature profile by replacing the inert pellets of Chalderbank et al, with a coaxial inert body which makes the cross section, taken up by the active catalyst pellets, annular and variable along the axial co-ordinate. In a theoretical example, based upon their reduction of a mathematical model into a one-dimensional form, for an irreversible exothermic reaction of A+B going to C with B in large excess, a complex longitudinal profile of an axial inert body is shown as a graph. According to their mathematical analysis, the complex longitudinal profile derived for the axial inert body should, in theory at least, realize a constant longitudinal temperature profile. Where a typical commercial reactor for a highly exothermic conversion contains up to 20,000 or even 30,000 contact tubes which are long relative, e.g., 100 to 250 times their diameter, there remain unsolved mechanical problems involving fabrication and/or maintenance of a coaxial inert body in each tube, as well as in loading catalyst into an annular space from the end with smallest dimension.

Other methods of obtaining a predetermined temperature profile along the axial co-ordinate of flow reactor containing a fixed heterogeneous catalyst is a quench-type reactor wherein cold fluid, such as fresh an/or recycled reactant, is injected into the flow at a plurality of points along the axial co-ordinate or between a plurality of catalyst beds. However, in a paper titled "Technology of Lurgi's Low Pressure Methanol Process" (CHEMTECH, July, 973, pp. 430-435) author E. Supp demonstrates that for methanol production from carbon oxides and hydrogen the tubular reactor with boiling water around the tubes provides more constant temperatures than does a quench-type reactor. Moreover, the temperature profile on the tubular reactor drops toward the outlet and thus contributes to a better equilibrium, while each stage of the quench-type reactor has an increasing temperature profile.

German Patent No. 29 29 300 describes a catalytic reactor, for use in carrying out endothermic or exothermic reactions, through which a reactant fluid is flowed, and containing a reaction chamber filled with catalyst material, which is in thermal contact with a heat-emitting or heat-absorbing fluid, and characterized by the fact that the cross-section surface area of the reaction chamber is varied, along with the direction of flow of the reacting fluid, depending upon the quantity of heat required for completion of a given reaction, or the quantity of heat released on the course of a reaction. For a proposed methanol synthesis reactor, the diameter of the reaction chamber is varied along the direction of flow of the reacting fluid such that the diameter (in mm), is a constant, having a value of from 15 to 25, multiplied by the gas flow rate per reaction tube ($Nm^3/hr$) raised to the power of a constant having a value of from 0.12 to 0.22. As practical matter, the reaction chamber is made up of only from 2 to 5 sections of tubing having constant diameter.

Japanese Patent No. 61-54229 describes a chemical reactor for exothermic conversions to form methanol which reactor has of a vertical reaction column filled with a granulated solid catalyst material. Gases required for the reaction are introduced into the top section of the reactor, and establishes a downward flow of reaction gas through the interior of the reactor column. Heat evolved by the reaction is removed from the column by vaporization of water surrounding the column, which is at saturation temperature. The reaction column consists of several sections of varying column diameter. In particular, the diameter of the upper part of the reaction column, where a relatively large amount of reaction heat is produced, is comparatively small; while the diameter of the lower portion of the column, where less reaction heat is liberated, is larger.

There remains, therefore, a current need for improved flow reactor apparatus for using a fixed heterogeneous catalyst which is effective in reducing the magnitude of the exotherm, reducing thermal degradation of catalyst activity and/or mechanical failure of catalyst/support, and thereby avoiding interruptions in service.

Advantageously, such improved flow reactor would, by means of higher selectivity and/or conversion of organic compounds, assist in improving recovery of value added products.

SUMMARY OF THE INVENTION

The invention is improved flow reactors for exothermic chemical conversions using a fixed heterogeneous catalyst with means for control of the exotherm. Apparatus of this invention is for use in a process which includes conversions of organic compounds to value added products using a selective heterogeneous catalyst.

One aspect of this invention is at least one flow reactor comprising a plurality of walled conduits each having an outer surface disposed for contact with a heat-transfer medium, an inlet distribution manifold adapted for flow communication with a downstream manifold through channels formed by heterogeneous catalytic material disposed within each conduit during operation in a sequence of zones for catalyst having the same or different length along the longitudinal coordinate of the conduit and within each zone essentially uniform cross-section of the conduit measured in a plane perpendicular to the longitudinal coordinate thereby defining volume of the zone, and the sequence of zones comprising at least two zones such that each downstream zone has a larger or smaller cross-section than the contiguous upstream zone. Generally, flow reactors according to the invention, further comprise a shell adapted to maintain during operation the outer surface of each conduit predominantly in contact with a heat-transfer medium, and having an inlet in flow communication with an outlet for the heat-transfer medium. Preferably, the sequence of zones comprises at least three zones. Preferably, each downstream zone has a larger cross section than the contiguous upstream zone. Preferably, each downstream zone has a larger volume than the contiguous upstream zone.

Advantageously, in flow reactors according to invention, the cross-section of the conduit in each zone has a substantially circular form with a diameter such that the third power of the diameter is equal to the product of the volume and a geometric factor having values in a range from about 0.01 to about 0.50. Preferably the geometric factor of each downstream zone is larger than the contiguous upstream zone for the sequence of zones comprising at least three zones.

In once class of flow reactors according to the invention, the zones for catalyst have a total length along the longitudinal coordinate of at least 4 meters. Preferably in such flow reactors the cross-section of the conduit in each zone has a substantially circular form with a diameter such that the third power of the diameter is equal to the product of the volume and a geometric factor having values in a range from about 0.015 to about 0.100. More preferably, the geometric factor of each downstream zone is larger than the contiguous upstream zone for the sequence of zones comprising at least three zones.

In another class of flow reactors according to the invention, the zones for catalyst have a total length along the longitudinal coordinate of less than about 3 meters. Preferably in such flow reactors the cross-section of the conduit in each zone has a substantially circular form with a diameter such that the third power of the diameter is equal to the product of the volume and a geometric factor having values in a range from about 0.10 to about 0.30. More preferably, the geometric factor of each downstream zone is larger than the contiguous upstream zone for the sequence of zones comprising at least three zones.

Another aspect of this invention is a flow reactor comprising:
(i) a plurality of walled conduits each having an outer surface disposed for contact with a heat-transfer medium,
(ii) an inlet distribution manifold adapted for flow communication with a downstream manifold through channels formed by heterogeneous catalytic material disposed within each conduit during operation,
(iii) a sequence of zones comprising at least two zones, said zones comprising said walled conduits, wherein
    (a) the walled conduits within each zone have the same or different length measured along the longitudinal coordinate of the zone,
    (b) the walled conduits within each zone have essentially uniform cross-section measured in a plane perpendicular to the longitudinal coordinate thereby defining volume of the zone, and
    (c) in the sequence of zones, the total cross-sectional area of the conduits in each downstream zone varies from the prior upstream zone,
(iv) at least one crossover chamber in flow communication with the plurality of walled conduits of a downstream zone and the plurality of walled conduits of the prior upstream zone,
(v) a shell adapted to maintain during operation the outer surface the plurality of walled conduits of each zone predominantly in contact with a heat-transfer medium, and
(vi) the shell having an inlet in flow communication with an outlet for flow of the heat-transfer medium.

Preferably, the sequence of zones comprises at least three zones. Preferably, each downstream zone has a larger cross section than the contiguous upstream zone. Preferably, each downstream zone has a larger volume than the contiguous upstream zone.

One aspect of this invention is a process which includes exothermic chemical conversions of organic compounds to value added products using a selective heterogeneous catalyst in at least one flow reactor comprising a plurality of walled conduits each having an outer surface disposed for contact with a heat-transfer medium, an inlet distribution manifold adapted for flow communication with a downstream manifold through channels formed by heterogeneous catalytic material disposed within each conduit during operation in a sequence of zones having the same or different length along the longitudinal coordinate of the conduit and within each zone essentially uniform cross-section of the conduit measured in a plane perpendicular to the longitudinal coordinate thereby defining volume of the zone, and the sequence of zones comprising at least two zones such that each downstream zone has a larger or smaller cross-section than the contiguous upstream zone. Preferably, the sequence of zones comprises at least three zones. Preferably, each downstream zone has a larger cross section than the contiguous upstream zone. Preferably, each downstream zone has a larger volume than the contiguous upstream zone. Typically, flow reactors according to the invention, further comprise a shell adapted to maintain during operation the outer surface of each conduit predominantly in contact with a heat-transfer medium, and having an inlet in flow communication with an outlet for the heat-transfer medium.

A preferred class of processes of the invention include the exothermic chemical conversions of organic compounds to value added products which comprises oxidation of benzene or a hydrocarbon selected from the group consisting of n-butane, butene-1 and butadiene, to form maleic anhydride. One preferred process of the invention comprises oxidation of n-butane to form maleic anhydride by contacting n-butane at low (less than lower flammability concentration of 1.6 mole percent in air) concentrations in an oxygen-containing gas with a fixed catalyst comprising principally vanadium, phosphorus and oxygen. Advantageously, the catalyst is maintained at temperatures in a range from about 360° C. to about 530° C.

In a preferred process of the invention the cross-section of each downstream zone is from about 5 percent to about 125 percent larger than the cross-section of the contiguous upstream zone. Advantageously, the volume of each downstream zone is from about 5 percent to about 125 percent larger than the volume of the contiguous upstream zone. More preferably the cross-section of each downstream zone which has a larger cross-section than the cross-section of the contiguous upstream zone is larger by an amount such that during operation temperatures of the exotherm as measured along the centerline are no more than 50° C. higher than the heat-transfer medium temperature.

For a more complete understanding of the present invention, reference should now be made to the embodiments illustrated in greater detail and described below by way of examples of the invention.

BRIEF DESCRIPTION OF THE DRAWING

FIG. 1 illustrates a conventional prior art multi-tubular flow reactor, wherein the conduits are of constant diameter.

FIG. 2 illustrates a multi-tubular flow reactor, wherein each conduit is comprised of a plurality of zones and wherein each zone from inlet to outlet is of increasing cross-sectional area.

FIG. 3 illustrates a multi-tubular flow reactor, wherein each conduit is of continuously increasing cross-sectional area from inlet to outlet.

FIG. 4 illustrates a multi-tubular flow reactor, comprised of a plurality of zones wherein (i) all conduits in single zone are of constant cross sectional area, (ii) each zone is connected to the subsequent zone by a crossover chamber which will collect the flow from the previous zone and redistribute the flow to the conduits of the next zone, and (iii) the cross sectional area of each conduit in the zone varies from one zone to the next.

FIG. 5 illustrates a multi-tubular flow reactor, comprised of a plurality of zones wherein (i) the conduits are of constant cross sectional area in all zones, (ii) each zone is connected to the subsequent zone by a crossover chamber which will collect the flow from the previous zone and redistribute the flow to the conduits of the next zone, and (iii) the number of conduits in each zone varies such that the total cross-sectional area of all conduits in each zone varies from one zone to the next.

Figure 1:
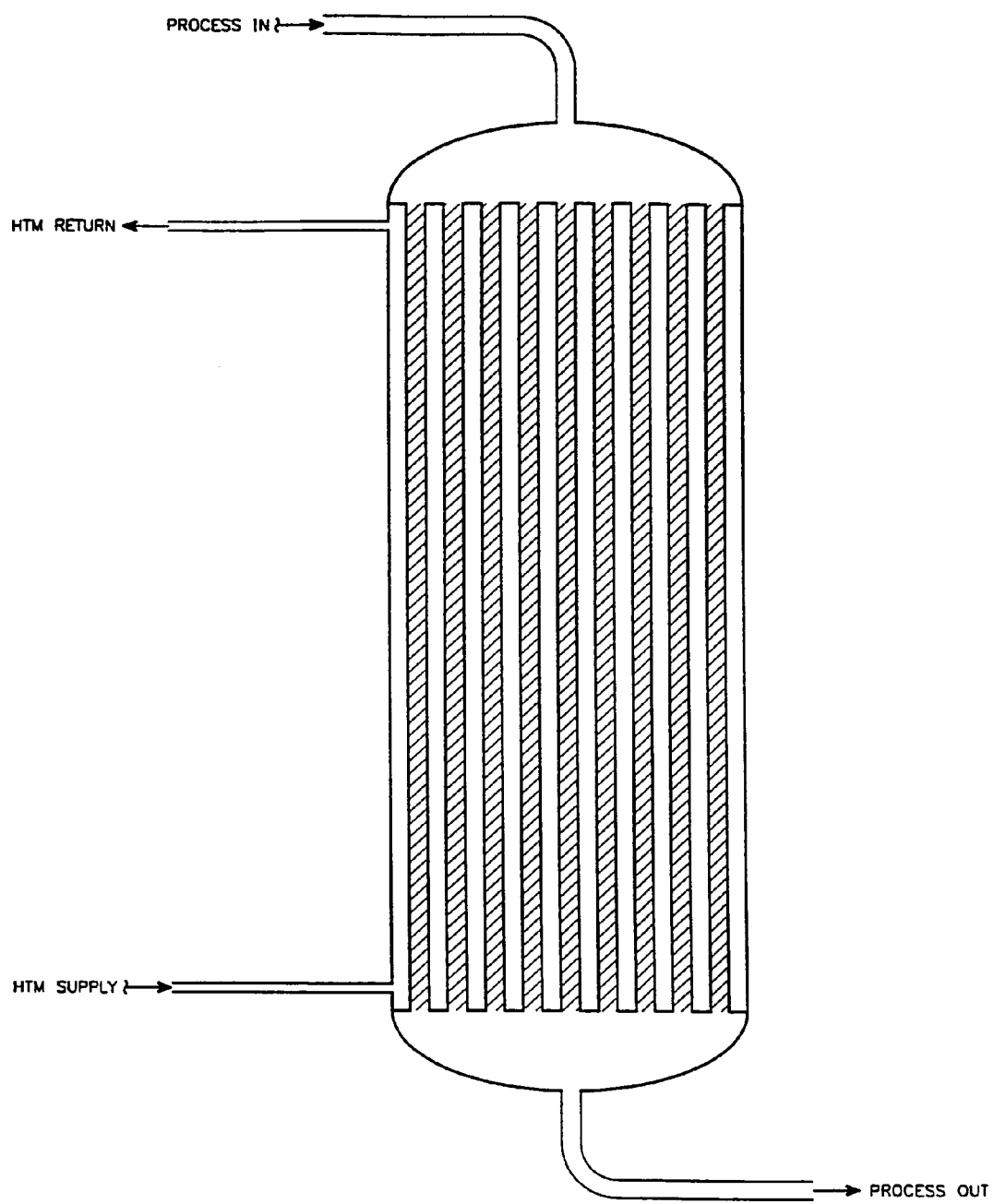
FIGS. 1 through 5 illustrate several variations of flow reactor design. In these figures the conduits (i.e. reactor tubes) connecting the inlet distribution manifold with the outlet manifold and typically packed with catalyst are represented by the shaded areas on the figures. The unshaded area surrounding the reactor tubes represent the area occupied by the heat transfer medium.

It will be understood by those skilled in the art that, as the drawing is diagrammatic, further items of equipment such as condensers, heat exchangers, reflux drums, column reboilers, pumps, vacuum pumps, temperature sensors, pressure sensors, pressure relief valves, control valves, flow controllers, level controllers, holding tanks, storage tanks, and the like, would additionally be required in a commercial plant. The provision of such additional items of equipment forms no part of the present invention and is in accordance with conventional chemical engineering practice.

The instant invention relates to a catalytic reactor, through which one or more reactants are flowed while undergoing exothermic reactions and conversion to at least one product, the catalytic reactor comprises a plurality of walled conduits each having an outer surface disposed for contact with a heat-transfer medium, and an inlet distribution manifold adapted for flow communication with a downstream manifold. Disposed within each conduit is a heterogeneous catalytic material which is in contact with the flow of reactants and reaction products during operation. Each conduit comprises a sequence of zones having the same or different length along the longitudinal coordinate of the conduit. Each zone is of essentially uniform cross-section of the conduit measured in a plane perpendicular to the longitudinal coordinate thereby defining volume of the zone. In the sequence of zones, each downstream zone has a different cross-section than the contiguous upstream zone. Typically, such reactors comprise at least two zones, preferably three zones. Preferably, the cross section of each zone is larger than the contiguous upstream zone. Preferably, each downstream zone has a larger volume than the contiguous upstream zone. Generally, flow reactors according to the invention, further comprise a shell adapted to maintain during operation the outer surface of each conduit predominantly in contact with the heat-transfer medium, and having an inlet in flow communication with an outlet for the heat-transfer medium.

Figure 2:
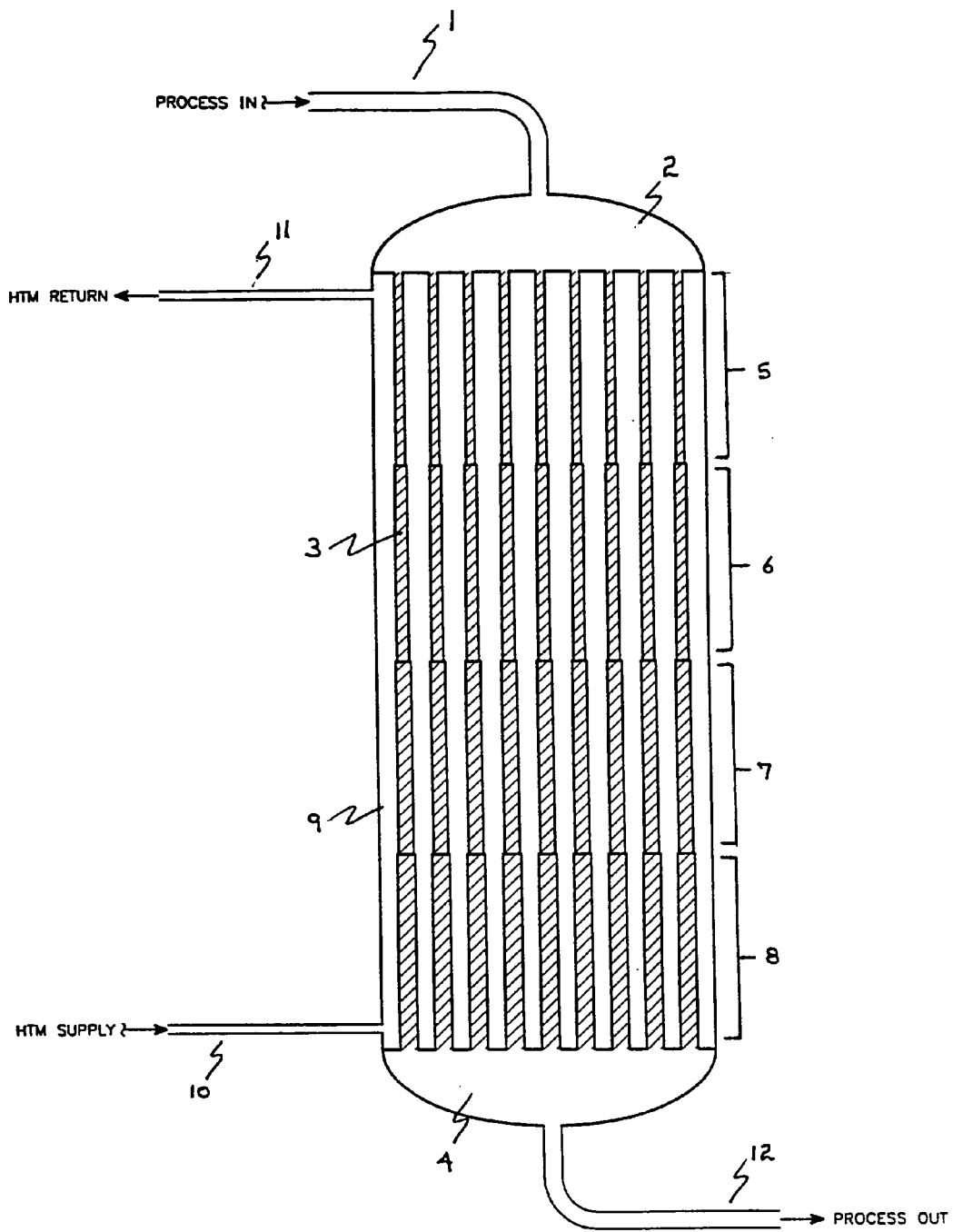

One embodiment of the invention is illustrated in FIG. 2. The reactants and any diluents are fed via one or more feed lines 1 into the inlet distribution manifold 2. The reactants and diluents pass through a plurality of conduits 3 to a downstream collection manifold 4. Each conduit comprises zones 5, 6, 7 and 8 of varying cross-section and length. The heat transfer medium (HTM) enters annular space 9 (i.e. the unshaded area) surrounding the conduit via line 10 and exits via line 11. The reactor effluent exits via line 12. In this figure, the conduits connecting the inlet distribution manifold with the outlet manifold contain catalyst and are represented by the shaded areas in the figure.

Figure 3:
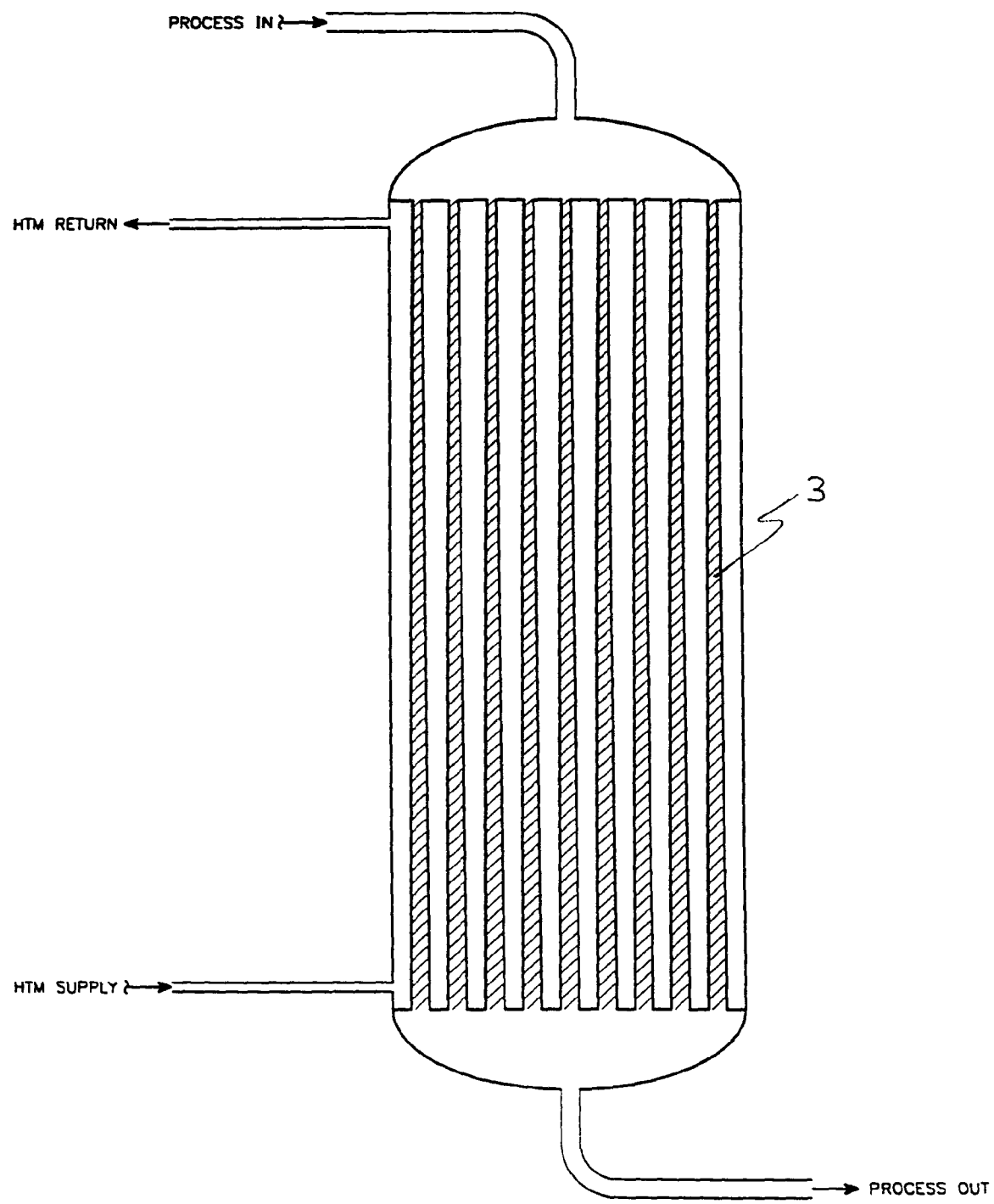

Another embodiment of this invention is illustrated in FIG. 3 wherein the conduits 3 are of gradually increasing cross section measured in a plane perpendicular to the longitudinal coordinate, as opposed to the step change in cross section from the prior zone shown in FIG. 2. The gradually increasing cross section of the conduits in FIG. 2 is essentially equivalent to an infinite number of zones.

Yet, another embodiment of this invention is a flow reactor comprising:
(i) a plurality of walled conduits each having an outer surface disposed for contact with a heat-transfer medium,
(ii) an inlet distribution manifold adapted for flow communication with a downstream manifold through channels formed by heterogeneous catalytic material disposed within each conduit during operation, (iii) a sequence of zones comprising at least two zones, said zones comprising said walled conduits, wherein
  (a) the walled conduits within each zone have the same or different length measured along the longitudinal coordinate of the zone,
  (b) the walled conduits within each zone have essentially uniform cross-section measured in a plane perpendicular to the longitudinal coordinate thereby defining volume of the zone, and
  (c) in the sequence of zones, the total cross-sectional area of the conduits in each downstream zone varies from the prior upstream zone,
(iv) at least one crossover chamber in flow communication with the plurality of walled conduits of a downstream zone and the plurality of walled conduits of the prior upstream zone,
(v) a shell adapted to maintain during operation the outer surface the plurality of walled conduits of each zone predominantly in contact with a heat-transfer medium, and
(vi) the shell having an inlet in flow communication with an outlet for flow of the heat-transfer medium.

Figure 4:
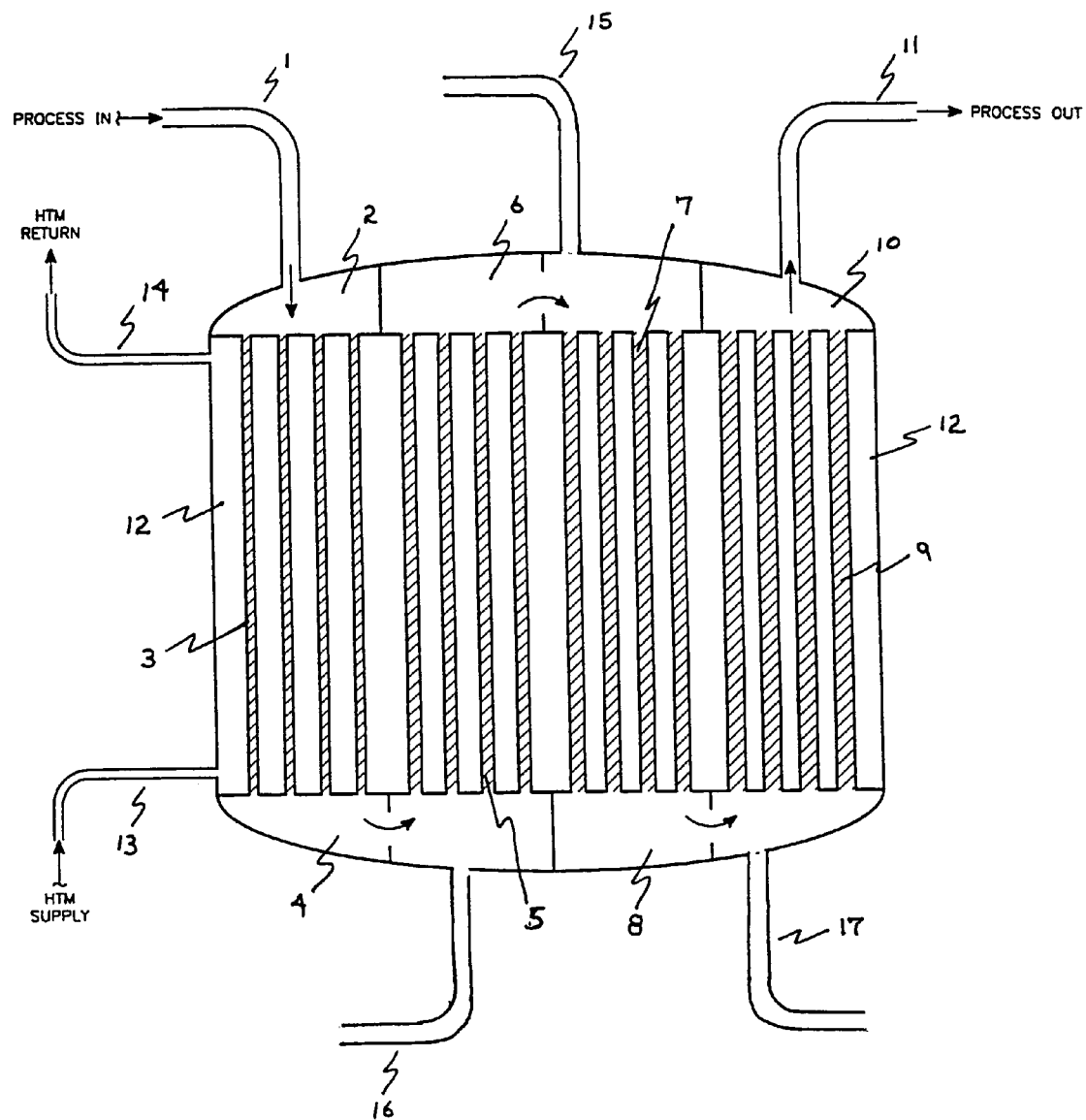
Figure 5:
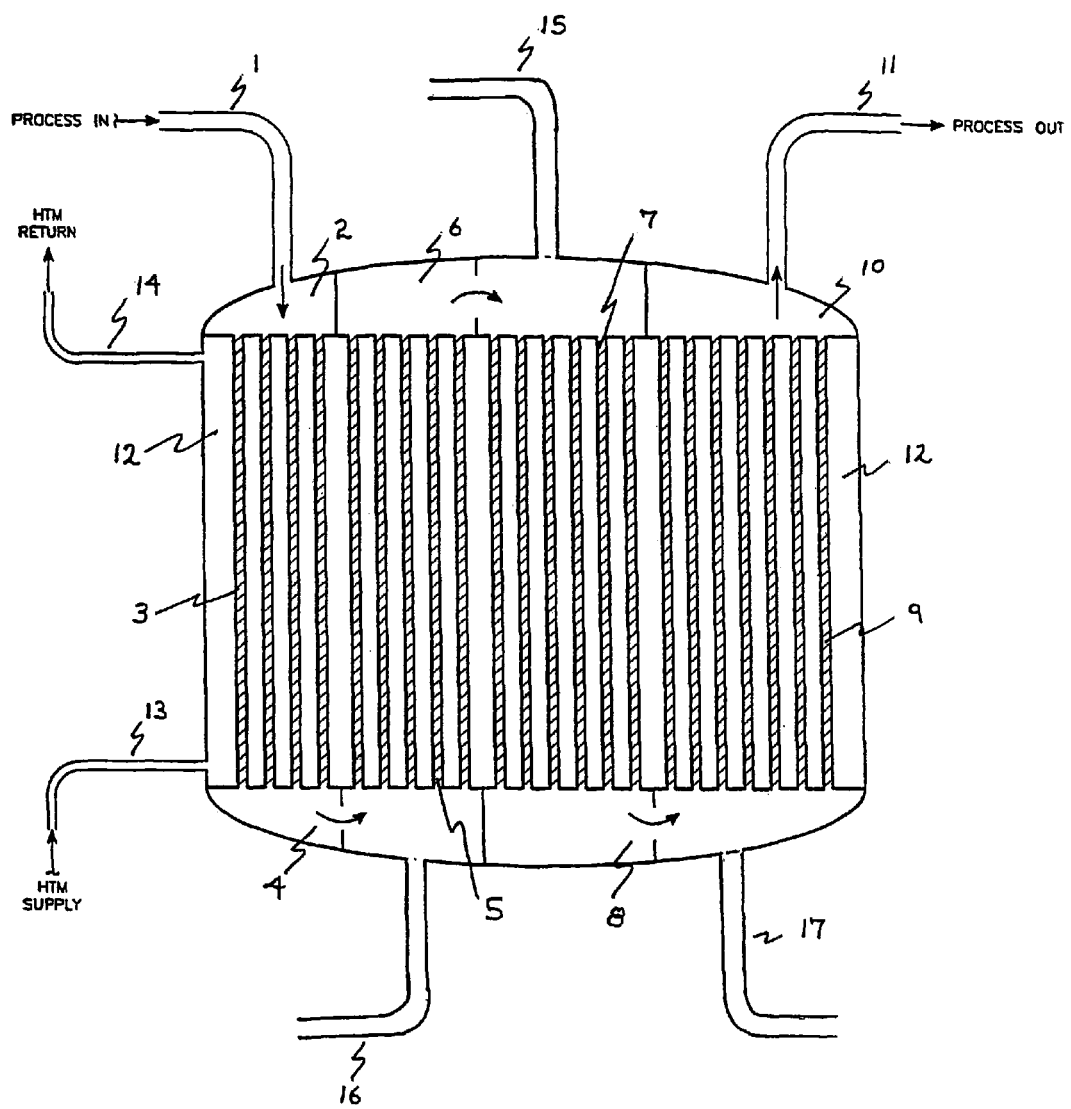

This embodiment of the invention is illustrated in FIGS. 4 and 5. The reactants and any diluents are fed via one or more feed lines 1 into the inlet distribution manual 2. The reactants and diluents pass through a plurality of catalyst containing conduits 3 in a first zone to a first crossover chamber 4. The reactants, any diluents and any reaction products from the previous zone flow pass from crossover chamber 4 through a plurality of catalyst containing conduits 5 in a second zone to a second crossover chamber 6. The reactants, any diluents and any reaction products from second zone pass from crossover chamber 6 through a plurality of catalyst containing conduits 7 in a third zone to a third crossover chamber 8. The reactants, any diluents and any reaction products from third zone pass from crossover chamber 8 through a plurality of catalyst containing conduits 9 in a fourth zone to an outlet manifold 10. The reactor effluent exits the reactor via line 11. The heat transfer medium enters annular space 12 (i.e. the unshaded) surrounding the conduits in each zone via line 13 and exits via line 14. Optionally, additional reactants and/or diluents may be introduced into one or more of the crossover chambers via lines 15, 16 or 17. In these figures, the catalyst containing conduits are represented by the shaded areas on the figures.

In FIG. 4, each zone contains an equal or different number of conduits with the cross section of each conduit increasing in each subsequent zone. In FIG. 5, the cross section of each individual conduit in all zones is constant, but the number of conduits varies in each zone such that the total cross sectional area of the conduits in each downstream zone increases from the prior upstream zone.

This latter embodiment of the invention may additionally be conducted in one or more reaction vessels connected in series, such that each reaction vessel comprises one or more zones. In this configuration, the crossover chamber comprises the collection and distribution manifolds at the bottom and top, respectively, of contiguous reaction vessels. Further, the reaction vessels could be operated with individual or common cooling loops (i.e. the flow path of the heat transfer medium). An "individual cooling loop" comprises a flow path for the heat transfer medium which passes through only one reaction vessel. In contrast, a "common cooling loop" comprises a flow path for the heat transfer medium, which passes through more than one reaction vessel.

A key feature in the design and utilization of the flow reactors described herein is to control the residence time of the reactants in each zone by varying both the cross sectional area and the length of each zone (thereby varying the volume of each zone) such that the heat generated during the exothermic reaction(s) occurring in the conduits in each zone does not exceed the amount of heat capable of being transferred to and removed by the heat transfer medium in the annular space surrounding the conduits. Flow reactors designed and operated in this fashion essentially "control" the extent of the reaction occurring in each zone to the extent that the formation of "hot spots", "runaway reactions", and/or reactor instability can be avoided.

As illustrated in the Figures, the total cross section of the conduits increases from the prior upstream zone. However, this invention also contemplates reactor designs wherein the total cross section of the conduits in a given zone decreases from the prior upstream zone.

Advantageously, in flow reactors according to invention, the cross-section of the conduit in each zone has a substantially circular form with a diameter such that the third power of the diameter is equal to the product of the volume and a geometric factor having values in a range from about 0.01 to about 0.50. Preferably the geometric factor of each downstream zone is larger than the contiguous upstream zone for the sequence of zones comprising at least three zones.

In one class of flow reactors according to the invention, the zones for catalyst have a total length along the longitudinal coordinate of at least 4 meters. Preferably in such flow reactors the cross-section of the conduit in each zone has a substantially circular form with a diameter such that the third power of the diameter is equal to the product of the volume and a geometric factor having values in a range from about 0.015 to about 0.100. More preferably, the geometric factor of each downstream zone is larger than the contiguous upstream zone for the sequence of zones comprising at least three zones.

In another class of flow reactors according to the invention, the zones for catalyst have a total length along the longitudinal coordinate of less than about 3 meters. Preferably in such flow reactors the cross-section of the conduit in each zone has a substantially circular form with a diameter such that the third power of the diameter is equal to the product of the volume and a geometric factor having values in a range from about 0.10 to about 0.30. More preferably, the geometric factor of each downstream zone is larger than the contiguous upstream zone for the sequence of zones comprising at least three zones.

Generally in multi-tubular fixed-bed reactors, reacting gas pass through the tubes, while a suitable heat transfer medium or coolant on the outside of the tubes removes the heat of reaction. Tube diameter is commonly from about 3 to about 5 centimeters; because greater diameters might give insufficient area for heat removal and lead to excessive hot spot temperatures in the center of the tube. Typical tube lengths range up to about 20 meters, however tube length may be limited to about 15 meters or less; because longer tubes may give unacceptably high-pressure drop.

With all multi-tubular fixed bed reactors, uniform flow through the tubes is important in achieving optimum performance. Uniform flow is especially important for exothermic reactors. If flow is slower through some tubes, heat removal is impaired, and local temperature spikes can lead to excessive production of undesired side products, e.g. oxides of carbon, in those tubes. If flow through some of the tubes is faster than average, the reduced residence time leads to lower conversions of reactants in those tubes. Flow rate depends on the resistance in the tubes, which is determined largely by the packed density of the catalyst. Procedures have been developed to load the catalyst pellets uniformly, with minimum breakage and dust formation. Some operators use preweighed bags of catalyst that they empty one by one into the tubes. Regardless of the loading method, the flow through each tube should be gauged by measuring the pressure drop under standard conditions. Tubes whose pressure drop is statistically lower or higher than the average should be emptied and refilled.

This invention also comprises a process for oxidizing benzene or hydrocarbons containing four carbon atoms such as n-butane, butene-1, and butadiene to maleic anhydride using at last one oxidation reactor comprising a plurality of walled conduits according to the invention. Maleic acid, cis-butenedioic acid, and fumaric acid, trans-butenedioic acid are important examples of unsaturated dicarboxylic acids. Preferably, maleic anhydride is produced by catalytic oxidation of n-butane according to the simple chemical equation:

$$CH_3CH_2CH_2CH_3 + 3.5O_2 => C_4H_2O_3 + 4H_2O$$

The main side reaction is the oxidation of n-butane to carbon oxides:

$$CH_3CH_2CH_2CH_3 + 5.5O_2 => 2CO_2 + 2CO + 5H_2O$$

While the ratio of carbon monoxide to carbon dioxide is shown as 1:1, obviously the ratio depends on catalyst and conditions of reaction. Both reactions are well known to be highly exothermic.

Catalyst selection depends somewhat on the particular hydrocarbon feed. For a feed of benzene, a catalyst comprising chiefly of molybdenum, vanadium and oxygen is preferred for best results, but for n-butane, a catalyst comprising mainly of phosphorus, vanadium, and oxygen, is preferred for best results. With a feed of unsaturated hydrocarbon containing about four carbon atoms, a catalyst comprising principally tungsten, phosphorus and oxygen is likely to show good results.

Generally contacting the hydrocarbon in the presence of oxygen with the catalyst is conducted at temperatures in a range from about 360° C. to about 530° C., but preferably not over about 450° C. The oxidation of n-butane to form maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 0.2 to about 1.7 mole percent of the hydrocarbon such as benzene, butane, butene, or butadiene. About 0.8 to about 1.5 mole percent of the hydrocarbon is satisfactory for optimum yield of maleic anhydride for the process of this invention. Although higher concentrations may be employed, explosive hazards may be encountered. Lower concentrations of the hydrocarbon feedstock, less than about one percent, of course, will reduce the total yield obtained at equivalent flow rates and, thus, are not normally employed for economic reasons. The flow rate of the gaseous stream through the reactor may be varied within rather wide limits, but the preferred range of operations is at the rate of about 100 to about 4000 cc of feed per cc of catalyst per hour and more preferably about 1000 to about 2400 cc of feed per cc of catalyst per hour. Lower flow rates make the butane oxidation process uneconomical. A catalyst should be effective at flow rates of about 1200 to about 2400 cc of hydrocarbon feed per cc of catalyst per hour. There are catalysts which show good promise but when subjected to the hourly space velocity designated above show very poor yields. The amount of water added is about 1000 to about 40,000 parts per million by weight of the reactor feed gas stream. The preferred amount of water added is about 5000 to about 35,000 parts per million by weight of the reactor feed gas stream. Residence times of the gas stream will normally be less than about four seconds, more preferably less than about one second, and down to a rate where less efficient operations are obtained. The flow rates and residence times are calculated at standard conditions of 760 mm of mercury and at 0° C.

A variety of reactors will be found to be useful and multiple tube heat exchanger-type reactors are quite satisfactory. The tubes of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium is needed to conduct heat from the reactors, such as lead and the like, but it has been found that eutectic salt baths are completely satisfactory. One such salt bath is a sodium nitrate, sodium nitrite, and potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as Vycor, and the like. Both carbon steel and nickel tubes have excellent long life under the conditions of the reaction described herein. Normally, the reactors contain a preheat zone containing an inert material such as one-quarter inch $Al_2O_3$ (Alundum™) pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other medium is to conduct heat away from the walls of the reactor and control the reaction. Better operations are normally obtained when the reaction temperature employed is no greater than about 10 to about 30° C. above the salt bath temperature. The temperature of the reactor, of course, will also depend to some extent upon the size of the reactor and hydrocarbon feedstock concentration.

The reaction may be conducted at atmospheric, superatmospheric or below atmospheric pressure. Typically, the reaction is conducted at superatmospheric pressure so that the exit pressure will be at least slightly higher than the ambient pressure to ensure a positive flow from the reactor. The pressure of the inert gases must be sufficiently higher to overcome the pressure drop through the reactor.

Maleic anhydride may be recovered by a number of ways well known to those skilled in the art. For example, the recovery may be by direct condensation or by adsorption in suitable media, with specific operation and purification of the maleic anhydride.

The following examples will serve to provide a fuller understanding of the invention, but it is to be understood that these examples are given for illustrative purposes only and should not be interpreted as limiting the invention in any way.

This invention includes processes for oxidation of o-xylene to phthalic anhydride using at least one oxidation reactor comprising a plurality of walled conduits according to the invention. Preferably, phthalic anhydride is produced by catalytic oxidation of o-xylene at from about 350° C. to about 400° C. with a solid catalyst, such as a vanadium-titanium oxygen catalyst according to the simple chemical equation:

$$1,2-(CH_3)_2C_6H_4+3O_2 \Rightarrow C_6H_4=1,2-(CO)_2O+3H_2O$$

The main side reaction is the complete oxidation of o-xylene. These oxidation reactions are well known to be highly exothermic.

This invention also comprises a process for oxidation of ethylene to ethylene oxide using at least one oxidation reactor comprising a plurality of walled conduits according to the invention. Preferably, ethylene oxide is produced by catalytic oxidation of ethylene with silver supported on a silica carrier along with some aluminum oxide according to the simple chemical equation:

$$2CH_2CH_2+O_2 \Rightarrow 2O(CH_2)_2$$

The main side reaction is the complete oxidation of ethylene:

$$CH_2CH_2+3O_2 \Rightarrow 2CO_2+2H_2O$$

Both reactions are well known to be highly exothermic.

While the conditions for oxidation of ethylene to ethylene oxide include temperatures not exceeding about 250° C. the heat of reaction is usually removed by boiling water on the outside of the tubes. At temperatures of reaction exceeding about 250° C., the liquid coolant boiling on the outside of the tubes is a hydrocarbon.

As it forms, the vapor leaves the reactor shell and is externally condensed (thus generating steam). Liquid coolant is returned to the reactor shell, preferably by gravity, to avoid reliance on a pump that could fail. The main advantage of using a refinery fraction boiling in the kerosene range is that the pressure on the shell side of the reactor is less than about 3 bar. The disadvantage is that the coolant is flammable.

The temperature in the reactor tubes is maintained at the desired level by automatically adjusting the pressure of the boiling coolant on the outside of the tubes. Turbulent mixing of the coolant is required to minimize radial variations in the reactor temperature and to provide a high heat-transfer coefficient. However, the temperature is not uniform along the length of the tubes: Near the top of the tubes, the temperature rises rapidly (the "hot spot"), then drops again to a nearly uniform temperature for the last 60-65 percent of the tube length.

Avoiding a temperature that is too high at the hot spot is important; high temperatures cause lower selectivity to ethylene oxide because more of the ethylene is burned to carbon dioxide and water. Moreover, the exothermic heat of reaction is much higher for carbon dioxide formation, and can exceed the local heat removal capacity of the coolant (a "runaway reaction"). This accelerating reaction must be avoided.

Reactor pressure can range from about 1 to about 30 bar, but is typically about 15 to about 25 bar. The pressure is chosen with regard to safety, handling, equipment, and other practical considerations. Higher pressures permit the use of smaller equipment to handle a given production rate. However, the flammable limit envelope expands somewhat at higher pressures, thereby reducing design options for selecting an operating point that is sufficiently removed from the unsafe operating region.

Typically the gas hourly space velocity is in a range of about 2500 to about 7000 hr$^{-1}$. Gas hourly space velocity (GHSV) is the volume of gas (measured at standard conditions) that passes through each volume of catalyst bed per hour.

This invention also comprises a process for preparation of acrylic acid by oxidation of propylene using at least one oxidation reactor comprising a plurality of walled conduits according to the invention. Typically, the catalytic vapor phase oxidation of propylene is carried out in two stages, i.e., oxidation of propylene to acrolein and acrylic acid, and oxidation of acrolein to acrylic acid.

In the first stage of catalytic oxidation, propylene is reacted according to the simple chemical equipments:

$$CH_2CHCH_3+O_2 \Rightarrow CH_2CHCOH+H_2O$$

and $$2CH_2CHCH_3+3O_2 \Rightarrow 2CH_2CHCOOH+2H_2O$$

The main side reactions are oxidation of propylene to carbon oxides:

$$2CH_2CHCH_3+7.5O_2 \Rightarrow 3CO+3CO_2+6H_2O$$

and formation of acetic acid:

$$CH_2CHCH_3+2.5O_2 \Rightarrow CH_3COOH+CO_2+H_2O$$

The main reaction in the second oxidation, acrolein to acrylic acid, is shown below:

$$2CH_2CHCOH+5.5O_2 \Rightarrow 3CO+3CO_2+4H_2O$$

These oxidation reactions are well known to be highly exothermic.

Generally, processes of the invention are divided into an oxidation section and a purification section. In the oxidation section, propylene is catalytically oxidized with air to acrolein (mainly) in the first stage, and to acrylic acid by further air oxidation of the intermediate mixture in the second stage. One or both oxidation reactions are carried out in at least one fixed bed oxidation reactor comprising a plurality of walled conduits according to the invention. In the purification section, the gaseous reactor effluent is cooled by direct contact with water, and acrylic acid is absorbed by the water. The aqueous acrylic acid solution azeotropically distilled with, for example, methyl isobutyl ketone, which forms an azeotrope with water and thus removes the water from the product stream. Beneficially, the crude acrylic acid is purified in a continuous two-column system to remove the light and heavy ends.

According to one embodiment of the invention liquid propylene (95 percent by weight propylene and 5 percent by weight propane), stored under pressure, is vaporized and mixed with compressed hot air. Advantageously, steam at elevated pressure up to about 250 psia is used as a diluent in the feed for better reactor operation. The feed mixture may be preheated before it enters one or more first stage oxidation reactor. The tubes are packed with a solid oxidation catalyst, for example a molybdenum-bismuth-tungsten mixed oxide catalyst. Molten salt on the shell side acts as a coolant, which is used to generate medium pressure steam in salt bath coolers. Typically, the pressure drop across the reactor tubes is less than about 20 psi. preferably less than about 10 psi. Effluents from each of the first-stage oxidation reactors are mixed with additional compressed hot air and medium pressure steam. The mixture is preheated to the reaction temperature before it enters the second-stage oxidation reactors, where the acrolein is oxidized to acrylic acid.

Preferably, the second-stage oxidation reactors are also shell-and-tube design comprising a plurality of walled conduits according to the invention, with a molybdenum-vanadium mixed oxide catalyst in the tubes and molten salt in the shell. Again the molten salt is used to generate medium pressure steam in salt bath coolers. Typically, the pressure drop across the reactor tubes is less than about 20 psi. preferably less than about 10 psi.

The gaseous product streams from each of the second-stage oxidation reactors are fed to a quench absorber near the bottom of the absorber. Water is used to quench the product mixture and absorb the acrylic acid, unreacted acrolein, acetic acid, and other nonvolatile by-products. Gases such as CO, CO2, O2, N2, steam, propane, and unreacted propylene exit the top of the absorber.

The gaseous acrylic acid solution leaving the bottom of the quench absorber is cooled and partially recycled to the top of the column as the liquid absorbent. A polymerization inhibitor, such as hydroquinone, is added to the system through the recycled absorbent stream. The aqueous product, which typically contains about 40 percent by weight of acrylic acid enters the purification section of the process as feed to the azeotropic distillation column.

In another embodiment, this invention includes processes for the oxyacetylation of ethylene to produce vinyl acetate monomer using at least one oxidation reactor comprising a plurality of walled conduits according to the invention. Preferably, vinyl acetate monomer is produced by catalytic oxyacetylation of ethylene at temperatures of from about 150° C. to about 200° C. with a solid catalyst, such as a silica support impregnated with palladium, gold and potassium acetate catalyst according to the simple chemical equation:

2(CH$_2$)$_2$+2CH$_3$COOH+O$_2$=>2CH$_3$COOCH+2H$_2$O

The main side reaction is the complete oxidation of reactants. These oxidation reactions are well known to be highly exothermic.

In yet another embodiment, this invention includes processes for the oxychlorination of ethylene to produce ethylene dichloride (1,2-dichloroethane) using at least one oxidation reactor comprising a plurality of walled conduits according to the invention. Preferably, ethylene dichloride is produced by catalytic oxychlorination of ethylene in the gas phase at from about 200° C. to about 250° C. with a solid catalyst, for example, cupric chloride with or without other active ingredients, impregnated on a porous support such as alumina, alumina-silica, or diatomaceous earth, preferably alumina, according to the simple chemical equation:

2(CH$_2$)$_2$+4HCl+O$_2$=>2CH$_2$Cl-CH$_2$Cl+2H$_2$O

Among the additives, alkaline metal chlorides are most useful preferably chlorides of potassium, lithium or sodium (KCl, LiCl, or NaCl). The main side reaction is the complete oxidation of reactants. These oxidation reactions are well known to be highly exothermic.

In view of the features and advantages of the method and apparatus for exothermic chemical conversions of organic compounds to value added products in accordance with this invention as compared to other flow reactors previously proposed and/or employed for control of the exotherm in vapor-phase processes using a fixed heterogeneous catalyst, the following examples are given.

EXAMPLES

The test program evaluated each reactor tube configuration for the highly exothermic chemical conversions in the making of maleic anhydride by oxidation of n-butane. In the example, the terms "conversion", "selectivity", and "yield" are defined as follows:

$$\text{Conversion (\%)} = \frac{\text{Moles n-butane consumed}}{\text{Moles n-butane in feed}} \times 100$$

$$\text{Selectivity (\%)} = \frac{\text{Moles maleic anhydride produced}}{\text{Moles n-butane consumed}} \times 100$$

$$\text{Yield (Wt. \%)} = [\text{Conversion (\%)}] \times [\text{Selectivity (\%)}] \times 169$$

The following demonstrations employed a pilot-scale flow reactor containing a fixed heterogeneous catalyst for continuous vapor-phase oxidation of n-butane with air. The pilot-scale system included a 48-inch reactor tube which was immersed in a heat transfer medium comprising of molten salt. The reactor tube was equipped with a ⅛-inch axial thermowell which allowed determination of the temperature profile of the catalyst bed along the axial co-ordinate. In each example a suitable amount of fresh commercial catalyst, i.e., a vanadium-phosphorus-molybdenum-oxygen catalyst, was charged to the reactor tube.

Comparative Example A

In this example the test program described above was used to evaluate a cylindrical reference reactor having a uniform cross-section of 5.07 cm² as measured in a plane perpendicular to the centerline and a catalyst zone volume of about 618 cm³. Concentration of butane in the feed was 1.5 mole percent. At 2000 VHSV in the catalyst zone and a molten salt temperature of 419° C., the maleic anhydride yield was 65 percent by weight after the catalyst was fully activated. The temperature profile of the catalyst bed along the axial co-ordinate exhibited a maximum of 471° C.

Example 1

In this example the test program described above was used to demonstrate a reactor having a volume for catalyst of about 613 cm³ distributed according to the invention into four contiguous cylindrical zones as shown in Table 1.

TABLE 1

| Catalyst Zone | Tube Length | Tube I.D. | Fraction of Axial Length | Percent of Total Catalyst Volume | Geometric Factor × 10² |
|---|---|---|---|---|---|
| I | 14 in. | 0.81 in. | 0.2917 | 19.28 | 7.37 |
| II | 12 in. | 0.87 in. | 0.2500 | 19.07 | 9.23 |
| III | 12 in. | 0.98 in. | 0.2500 | 24.29 | 10.42 |
| IV | 10 in. | 1.33 in. | 0.2083 | 37.36 | 16.99 |

Concentration of butane in the feed was 1.5 mole percent. At 2000 VHSV in the catalyst zone and a molten salt temperature of 395° C., the maleic anhydride yield was 91 percent by weight after the catalyst was fully activated. The temperature profile of the catalyst bed exhibited a maximum of 446° C.

Example 2

In this example the test program described above was used to demonstrate a reactor having a volume for catalyst of about 620 cm³ distributed according to the invention into four contiguous cylindrical zones as shown in Table II.

TABLE II

| Catalyst Zone | Tube Length | Tube I.D. | Fraction of Axial Length | Percent of Total Catalyst Volume | Geometric Factor × $10^2$ |
|---|---|---|---|---|---|
| I | 14 in. | 0.81 in. | 0.2917 | 19.28 | 7.37 |
| II | 14 in. | 0.87 in. | 0.2917 | 22.01 | 7.91 |
| III | 14 in. | 1.12 in. | 0.2917 | 36.74 | 10.22 |
| IV | 6 in. | 1.33 in. | 0.1250 | 22.18 | 28.31 |

Concentration of butane in the feed was 1.5 mole-percent. At 2000 VHSV in the catalyst zone and a molten salt temperature of 389° C., the maleic anhydride yield was 90 percent by weight after the catalyst was fully activated. The temperature profile of the catalyst bed exhibited a maximum of 426° C.

Example 3

In this example the test program described above was used to demonstrate a reactor having a volume for catalyst of about 616 cm³ distributed according to the invention into four contiguous cylindrical zones as shown in Table III.

TABLE III

| Catalyst Zone | Tube Length | Tube I.D. | Fraction of Axial Length | Percent of Total Catalyst Volume | Geometric Factor × $10^2$ |
|---|---|---|---|---|---|
| I | 12 in. | 0.74 in. | 0.2500 | 14.64 | 7.91 |
| II | 12 in. | 0.87 in. | 0.2500 | 18.98 | 9.23 |
| III | 13 in. | 1.12 in. | 0.2708 | 26.19 | 9.62 |
| IV | 11 in. | 1.33 in. | 0.2292 | 40.19 | 15.44 |

Concentration of butane in the feed was 1.5 mole percent. At 2000 VHSV in the catalyst zone and a molten salt temperature of 384° C. The maleic anhydride yield was 89 percent by weight after the catalyst was fully activated. The temperature profile of the catalyst bed exhibited a maximum of 455° C.

Example 4

In this example the test program described above was used to demonstrate a reactor having a volume for catalyst of about 620 cm³ distributed according to the invention into four contiguous cylindrical zones as shown in Table IV.

TABLE IV

| Catalyst Zone | Tube Length | Tube I.D. | Fraction of Axial Length | Percent of Total Catalyst Volume | Geometric Factor × $10^2$ |
|---|---|---|---|---|---|
| I | 14 in. | 0.81 in. | 0.2917 | 19.08 | 7.37 |
| II | 14 in. | 0.87 in. | 0.2917 | 22.01 | 7.91 |
| III | 14 in. | 1.12 in. | 0.2916 | 36.74 | 10.22 |
| IV | 14 in. | 1.33 in. | 0.1250 | 22.18 | 28.31 |

Concentration of butane in the feed was 2.0 mole percent. At 2000 VHSV in the catalyst zone and a molten salt temperature of 383° C., the maleic anhydride yield was 81 percent by weight after the catalyst was fully activated. The temperature profile of the catalyst bed exhibited a maximum of 446° C.

Example 5

In this example the test program described above was used to demonstrate a reactor having a volume for catalyst of about 617 cm³ distributed according to the invention into four contiguous cylindrical zones as shown in Table V.

TABLE V

| Catalyst Zone | Tube Length | Tube I.D. | Fraction of Axial Length | Percent of Total Catalyst Volume | Geometric Factor × $10^2$ |
|---|---|---|---|---|---|
| I | 6 in. | 0.98 in. | 0.1250 | 12.07 | 20.83 |
| II | 15 in. | 0.87 in. | 0.3125 | 23.67 | 7.39 |
| III | 11 in. | 0.98 in. | 0.2292 | 22.11 | 11.37 |
| IV | 16 in. | 1.12 in. | 0.3333 | 42.15 | 8.94 |

Concentration of butane in the feed was 1.5 mole percent. At 2000 VHSV in the catalyst zone and a molten salt temperature of 384° C., the maleic anhydride yield was 79 percent by weight after the catalyst was fully activated. The temperature profile of the catalyst bed exhibited a maximum of 471° C.

The following demonstrations employed a mock-up of commercial flow reactor containing a fixed heterogeneous catalyst for continuous vapor-phase oxidation of n-butane with air. The mock-up system included a 4.6-meter reactor tube which was immersed in a heat transfer medium comprising of molten salt. The reactor tube was equipped with an axial thermowell which allowed determination of the temperature profile of the catalyst bed along the axial co-ordinate. In each example a suitable amount of fresh commercial catalyst, i.e., a vanadium-phosphorus oxygen catalyst, was charged to the reactor tube.

Comparative Example B

In this example the test program described above was used to evaluate a cylindrical reference reactor having a uniform cross-section in a plane perpendicular to the centerline and a catalyst zone of about 2,012 cm³. Concentration of butane in the feed was 1.7 mole percent. At 2000 VHSV in the catalyst zone and a molten salt temperature of 413° C., the maleic anhydride yield was 77 percent by weight after the catalyst was fully activated. The temperature profile of the catalyst bed along the axial co-ordinate exhibited a maximum of 491° C.

Example 6

In this example the test program described above was used to demonstrate a reactor having a volume for catalyst of about 617 cm³ distributed according to the invention into four contiguous cylindrical zones as shown in Table V.

TABLE VI

| Catalyst Zone | Tube Length | Tube I.D. | Fraction of Axial Length | Percent of Total Catalyst Volume | Geometric Factor × $10^2$ |
|---|---|---|---|---|---|
| I | 45 in. | 0.81 in. | 0.2486 | 15.75 | 2.69 |
| II | 56 in. | 0.87 in. | 0.3094 | 22.02 | 2.27 |
| III | 56 in. | 1.12 in. | 0.3094 | 38.16 | 2.77 |
| IV | 24 in. | 1.33 in. | 0.1326 | 24.07 | 7.49 |

Concentration of butane in the feed was 1.7 mole percent. At 2000 VHSV in the catalyst zone and a molten salt temperature of 396° C., the maleic anhydride yield was 96 percent by weight after the catalyst was fully activated. The temperature profile of the catalyst bed exhibited a maximum of 429° C.

For the purposes of the present invention, "predominantly" is defined as more than about fifty percent. "Substantially" is defined as occurring with sufficient frequency or being present in such proportions as to measurably affect macroscopic properties of an associated compound or system.

Where the frequency or proportions for such impact is not clear, substantially is to be regarded as about ten percent or more. "Essentially" is defined as absolutely except that small variations which have no more than a negligible effect on macroscopic properties and final outcome are permitted, typically up to about one percent.

That which is claimed is:

1. A flow reactor comprising:
   (i) a plurality of walled conduits each having an outer surface disposed for contact with a heat-transfer medium,
   (ii) an inlet distribution manifold in flow communication with a downstream manifold through channels formed by heterogeneous catalytic material disposed within each conduit during operation,
   (iii) a sequence of zones comprising at least two zones, said zones comprising said walled conduits, wherein
      (a) the walled conduits within each zone have the same or different length measured along a longitudinal coordinate of the zone,
      (b) the walled conduits within each zone have essentially uniform cross-section measured in a plane perpendicular to the longitudinal coordinate thereby defining volume of the zone, and
      (c) in the sequence of zones, the total cross-sectional area of the conduits in each downstream zone varies from the prior upstream zone,
   (iv) at least one crossover chamber in flow communication with the plurality of walled conduits of a downstream zone and the plurality of walled conduits of the prior upstream zone,
   (v) a shell for maintaining during operation the outer surface of the plurality of walled conduits of each zone predominantly in contact with a heat transfer medium, and
   (vi) the shell having an inlet in flow communication with an outlet for flow of the heat-transfer medium.

2. The flow reactor of claim 1, wherein the cross section and length of each zone are sized so that the heat generated during any exothermic reactions occurring inside the conduits of the zone does not exceed the amount of heat capable of being transferred to and removed by the heat transfer medium surrounding the conduits.

3. The flow reactor according to claim 1, wherein the sequence of zones comprises at least three zones.

4. The flow reactor according to claim 1, wherein that each downstream zone has a larger cross-section than the contiguous upstream zone.

5. The flow reactor according to claim 1, wherein each downstream zone has a larger volume than the contiguous upstream zone.

6. The flow reactor according to claim 1, wherein at least one crossover chamber has an inlet in flow communication with the plurality of walled conduits of a downstream zone.

7. The flow reactor according to claim 1, further comprising a shell for maintaining during operation the outer surface of each conduit predominantly in contact with a heat-transfer medium, and having an inlet in flow communication with an outlet for the heat-transfer medium.

8. The flow reactor according to claim 7, wherein cross section of the conduit in each zone has a substantially circular form with a diameter such that the third power of the diameter is equal to the product of the volume and a geometric factor having values in a range from about 0.01 to about 0.50.

9. The flow reactor according to claim 7, wherein the geometric factor of each downstream zone is larger than the contiguous upstream zone for the sequence of zones comprising at least three zones.

10. The flow reactor according to claim 1, wherein the zones for catalyst have a total length along the longitudinal coordinate of at least 4 meters.

11. The flow reactor according to claim 1, wherein the cross-section of the conduit in each zone has a substantially circular form with a diameter such that the third power of the diameter is equal to the product of the volume and a geometric factor having values in a range from about 0.015 to about 0.100.

12. The flow reactor according to claim 11, wherein the geometric factor of each downstream zone is larger than the contiguous upstream zone for the sequence of zones comprising at least three zones.

* * * * *